(12) United States Patent
Tolwani et al.

(10) Patent No.: US 8,147,698 B2
(45) Date of Patent: Apr. 3, 2012

(54) PROCESS FOR METABOLIC CONTROL AND HIGH SOLUTE CLEARANCE AND SOLUTIONS FOR USE THEREIN

(75) Inventors: Ashita Tolwani, Birmingham, AL (US); Rajesh Speer, Birmingham, AL (US); Brenda Stofan, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 13/010,770

(22) Filed: Jan. 20, 2011

(65) Prior Publication Data

US 2011/0230813 A1    Sep. 22, 2011

Related U.S. Application Data

(62) Division of application No. 11/273,290, filed on Nov. 14, 2005, now Pat. No. 7,884,132.

(51) Int. Cl.
| | |
|---|---|
| *B01D 61/24* | (2006.01) |
| *A61K 33/14* | (2006.01) |
| *A61K 33/00* | (2006.01) |
| *A61K 31/19* | (2006.01) |
| *A61M 1/14* | (2006.01) |

(52) U.S. Cl. ....... 210/647; 210/645; 210/646; 604/4.01; 604/5.01; 424/680; 514/557; 514/575

(58) Field of Classification Search ................ 210/645, 210/646, 647; 424/663, 677, 678, 679, 680, 424/681, 717; 514/575, 557; 604/4.01, 5.01

See application file for complete search history.

(56) References Cited

U.S. PATENT DOCUMENTS

| | | |
|---|---|---|
| 4,500,309 A | 2/1985 | Diederich et al. |
| 5,032,615 A | 7/1991 | Ward et al. |
| 6,566,402 B2 | 5/2003 | Warnock |
| 6,743,191 B1 | 6/2004 | Chang |
| 7,186,420 B2 | 3/2007 | Chang et al. |

(Continued)

FOREIGN PATENT DOCUMENTS

DE         41 14 908 A1    11/1992

(Continued)

OTHER PUBLICATIONS

Dorval, "A novel citrate anticoagulation regimen for continuous venovenous hemodiafiltration" *Intensive Care Med.* 29:1186, published online May 22, 2003.

(Continued)

*Primary Examiner* — John Kim

(74) *Attorney, Agent, or Firm* — Bradley Arant Boult Cummings LLP

(57) ABSTRACT

The present disclosure describes novel standardized citrate replacement fluid solutions and a standardized dialysate solution for use with CRRT methods. The standardized citrate replacement fluid solutions and standardized dialysate solutions do not require modification based on the clinical status of the individual patients. The use of the standardized solutions described herein offers significant advantages over the prior art solutions used in CRRT. The present disclosure describes superior metabolic and electrolyte control and significantly increased dialyzer patency in: (a) 24 intensive care unit (ICU) patients with ARF using a 0.67% trisodium citrate replacement fluid solution, and (b) 32 ICU patients with ARF using a 0.5% trisodium citrate replacement fluid solution. Both groups were treated with Bicarbonate-25 dialysate and achieved effluent rates of 35 mL/kg/hr.

41 Claims, 5 Drawing Sheets

U.S. PATENT DOCUMENTS

| | | |
|---|---|---|
| 7,544,301 B2 | 6/2009 | Shah et al. |
| 2002/0077580 A1 | 6/2002 | Tobe |
| 2003/0045827 A1 | 3/2003 | Nier et al. |

FOREIGN PATENT DOCUMENTS

| | | |
|---|---|---|
| JP | 2005 206572 A | 8/2005 |
| WO | 2005/002599 A1 | 1/2005 |

OTHER PUBLICATIONS

Mehta et al., "Regional citrate anticoagulation for continuous arteriovenous hemodialysis in critically ill patients." *Kidney Int* 38: 976 981. 1990.

Kutsogiannis et al., "Regional citrate anticoagulation in continuous venovenous hemodiafiltration." *AJKD* 35: 802-811. 2000.

Tobe, "A novel regional citrate anticoagulation protocol for CRRT using only commercially available solutions." *J Crit. Care* 18: 121-129. 2003.

Cointault "Regional citrate anticoagulation in continuous venovenous haemodiafiltration using commercial solutions." *Neph Dial Trans* 19:171-178. 2004.

Gabutti "Citrate anticoagulation in continuous venovenous hemodiafiltration: A metabolic challenge." *Intensive Care Med* 28:1419-1425. 2002.

Tolwani "A Practical Citrate Anticoagulation CVVHDF Protocol for Metabolic Control and High Solute Clearance." *Clin J Am Soc Nephrol.* 2005.

Vanholder "What is the renal replacement method of first choice for intensive care patients?" *J. Am. Soc. Nephrol.* 12: S40-S43. 2001.

Davies et al., A regional citrate anticoagulation protocol for pre-dilutional CVVHDF: The 'modified Alabama protocol') *Australian Critical Care* 21:154-166. 2008.

Bihorac at al., "Continuous venovenous hemofiltration with citrate-based replacement fluid: Efficacy, safety, and impact on nutrition" *Am. J. Kidney Diseases* 46(5):908-918. 2005.

European Patent Office (2010) Supplementary European Search Report.

ISA, Written Opinion of the International Searching Authority. May 19, 2009.

PROCESS FOR METABOLIC CONTROL AND HIGH SOLUTE CLEARANCE AND SOLUTIONS FOR USE THEREIN

The present application claims priority to and the benefit of U.S. non-provisional application Ser. No. 10/273,290, filed Nov. 14, 2005, now U.S. Pat. No. 7,884,132 B2.

FIELD OF THE DISCLOSURE

The present disclosure relates generally to the field of renal function and renal disease. The present disclosure relates specifically to the use of a defined dilute regional trisodium citrate solution during continuous renal replacement therapy for the treatment of renal disease.

BACKGROUND

Continuous renal replacement therapy (CRRT) is well established as a modality for the management of renal failure in the critically ill patient. When CRRT was first developed, the major indications for use were fluid and solute removal associated with renal failure, such as those patients developing acute renal failure (ARF). Acute renal failure (ARF) is rarely an isolated process but is often a complication of underlying conditions such as sepsis, trauma, and multiple-organ failure in critically ill patients. As such, concomitant clinical conditions significantly affect patient outcome. CRRT applications have developed over time to include use for patients with chronic renal failure (CRF) and for other indications. Continuous renal replacement therapy (CRRT) has recently emerged as the dialysis technique of choice for critically ill patients with acute renal failure (ARF). There are several types of CRRT therapy, including but not limited to, continuous venovenous hemofiltration (CVVH). CRRT is generally recognized as offering significant advantages to intermittent dialysis for fluid and metabolic control (1). Additionally, high ultrafiltration rates (greater than or equal to 35 ml/kg/hr) using CRRT, such as CVVH, have been associated with improved patient survival (2).

During CRRT procedures, solutions must be added to keep the blood flowing through the CRRT device from clotting. Heparin sodium is the most common anticoagulant used for CRRT. Systems are frequently flushed with dilute heparin through the system during the priming procedure (5,000-10,000 U/L normal saline) followed by a constant delivery of heparin for the duration of therapy. For many years, it was the anticoagulant of choice for all forms of dialysis that used a blood path. However, as CRRT was applied to the more profoundly ill patients, heparin was found to be associated with complications caused by coagulation disorders seen in the critically ill. Side effects that may be observed include, but are not limited to, systemic anticoagulation, thrombocytopenia and suppressed aldosterone secretion. The effects on systemic coagulation make heparin administration very problematic in patients with gastrointestinal bleeding or traumatic injury in which hemostasis is impaired due to coagulation factor consumption or occult bleeding from wounds or vascular puncture sites. Frequent monitoring of coagulation studies and platelet counts as well as continual monitoring for bleeding complications is essential for any patient undergoing heparin anticoagulation of the CRRT system. Patients do not require bolusing with heparin before initiation of therapy, because the goal is not to anticoagulate patients but rather to provide regional anticoagulation for the system. If the heparin used for priming is not thoroughly flushed from the system, patients will still receive a small heparin bolus from the priming volume.

Trisodium citrate has been used for many years as an anticoagulant for blood products. It was introduced to CRRT as a regional anticoagulant in the early 1990s. Relatively normal hepatic function is required to metabolize sodium citrate.

Therefore, trisodium citrate has been used to provide anticoagulation of blood in the extracorporeal circuit during CRRT. Citrate affects anticoagulation by binding with calcium and rendering calcium unavailable to the clotting cascade. Since several steps of the clotting cascade are dependent on calcium, the absence of calcium prevents clotting. Once the blood from the extracorporeal circuit is returned to the patient it mixes with the central venous blood which contains calcium and the anticoagulant effect is neutralized. In other words, citrate when returned to the patient from the extracorporeal circuit is no longer an anticoagulant. Generally, calcium is administered to the patient on a continuous basis to prevent any depletion of calcium stores which may occur as a result of citrate binding with calcium and loss of calcium through the extracorporeal circuit.

The prior art has recognized that complications may arise when using trisodium citrate as a regional anticoagulant. The toxicities of this approach include metabolic alkalosis due to citrate accumulation and its subsequent metabolism to bicarbonate, and the effects of reduced systemic ionized calcium. Subjectively the patient may experience palpitations, perioral tingling and stomach cramps. Objective features of citrate toxicity include myocardial depression, arrhythmias and systemic alkalosis which may or may not include an anion gap. Proper surveillance of the rate of citrate administration and monitoring and correction of systemic ionized calcium may obviate these effects. Since normal liver function is required for the metabolism of trisodium citrate, patients with liver disease may be prone to developing citrate toxicity and caution must be exercised in treating these patients with citrate.

Although the use of citrate for regional anticoagulation has been shown to be superior to heparin (4), it often complicates CRRT. A small number of regional citrate anticoagulation protocols offer high solute clearance but also require several customized solutions (5, 6, 7, 8, 9, 10). Customization of solutions, with subsequent adjustments based on or determined by patient clinical status, expends pharmacy resources in preparing the solutions and increases the risk of error in the preparation of the solutions and their administration (11). This customization of solutions can vary not only between individual patients, but can vary as to the same patient based on that patient's changing clinical status. In addition, if a patient's clinical status changes over the course of treatment, previously prepared solutions may have to be discarded, thereby increasing the costs of treatment. In 2004, two patients receiving CRRT died after potassium chloride, rather than sodium chloride, was mistakenly added to a custom-made dialysate (12, 13). As the FDA does not presently require batch testing for quality control, potentially hazardous CRRT solution errors may be unrecognized. In a recent international survey on the management of critically ill ARF patients, the greatest concerns with CRRT included anticoagulation, dialyzer clotting, nursing workload, lack of standards, and cost (3).

The ideal CRRT protocol should provide volume control, metabolic (acid-base and electrolyte) control, and adequate solute clearance, without significant complications related to bleeding or clotting and should be versatile to allow for independent adjustment of the above parameters. Furthermore, the CRRT protocol should use standardized solutions and should not require more than two or three different types of solutions in order to minimize the strain on the compounding pharmacy and healthcare providers. Finally, the CRRT should ideally run with little or no interruption.

The present disclosure provides novel solutions for use with CRRT. In one embodiment, the CRRT protocol is a continuous venovenous hemodiafiltration (CVVHDF) method. CVVHDF provides both diffusive and convective solute clearance and easily maintains a filtration fraction<20% at low blood flow rates and high effluent rates, thereby decreasing the likelihood of filter clotting (14). The present disclosure also provides a simplified set of CRRT solutions for use in CRRT.

Altering the composition of CRRT solutions for each patient proved to be costly, labor-intensive, and error-prone. As a result, we first devised a simplified citrate protocol using 2% trisodium citrate delivered as replacement fluid at 250 ml/hr (citrate 17.5 mmol/hr), with a standardized normal saline dialysate delivered at 1000 ml/hr (15). However, this method could not provide higher effluent rates without also causing severe metabolic complications.

In one embodiment, a bicarbonate-based dialysate and a dilute citrate solution used for both anticoagulation and replacement fluid are disclosed. The citrate solution provides adequate metabolic control, a high ultrafiltration rate, and effective regional anticoagulation without requiring customization based on the clinical status of an individual patient.

DETAILED DESCRIPTION

Figure 1A:
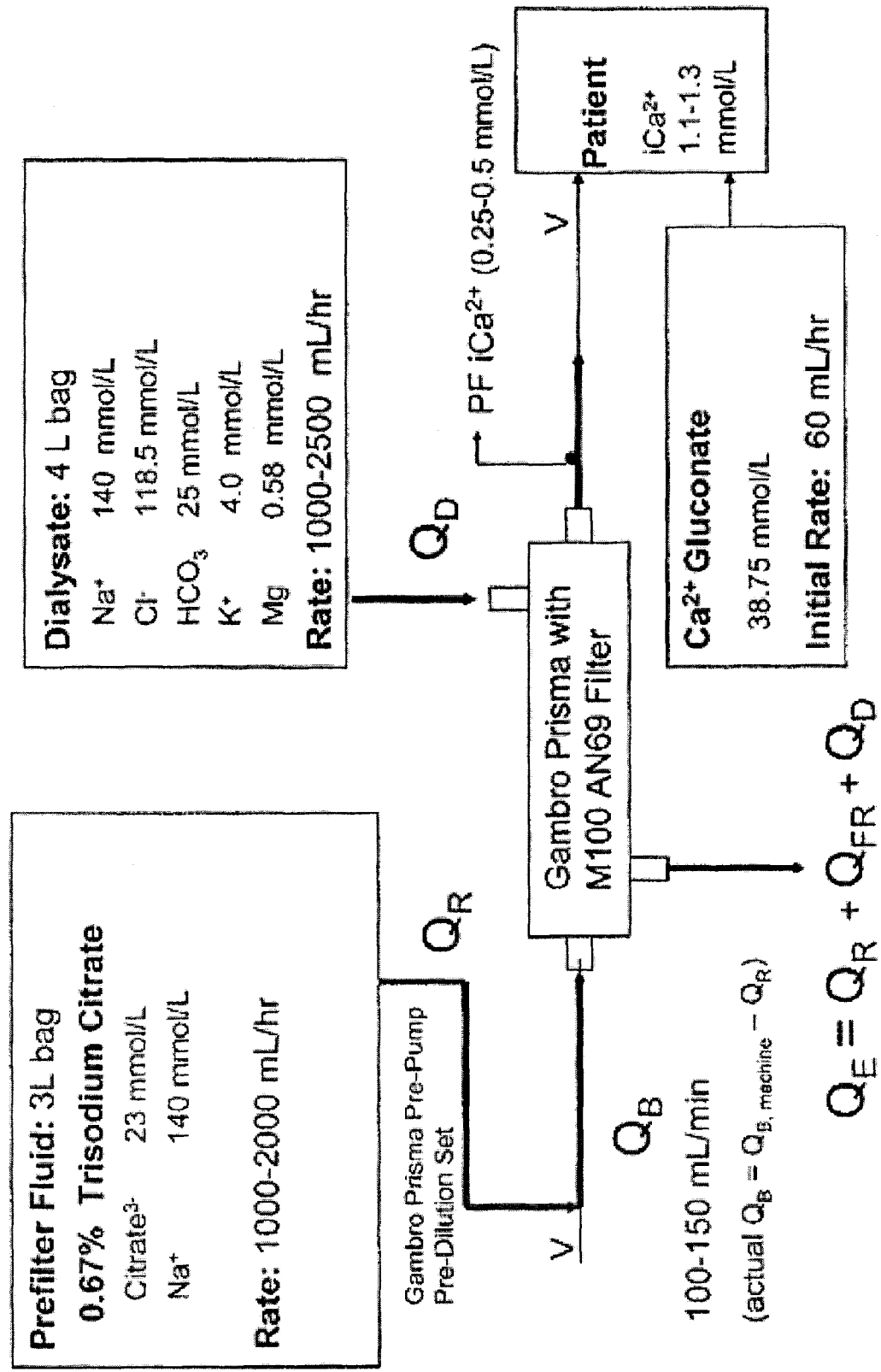
FIG. 1A shows one embodiment of a schematic diagram of the procedure for CVVHDF CRRT therapy using the 0.67% TSC solution as the replacement fluid solution and Bicarbonate-25 as the dialysate solution.

The present disclosure provides standardized solutions of dilute citrate as replacement fluid solution for use in CRRT protocols and further provides methods of using the citrate solution in CRRT protocols. The present disclosure describes a 0.67% trisodium citrate (TSC) solution and a 0.5% TSC solution as the citrate replacement fluid solution. The present disclosure also provides standardized solutions of dialysate and calcium for use in CRRT protocols and further provides methods of using the dialysate and calcium solutions in combination with the citrate replacement fluid solutions. The standardized solutions and methods of the preset disclosure are a practical and economical improvement over currently published CRRT protocols incorporating citrate solutions.

The prior art has recognized that citrate solutions could be used in CRRT methods. Prior art CRRT protocols utilizing citrate solutions required solutions customized to meet the needs of the individual patient in order to address metabolic and electrolyte requirements and often required further alterations during use as a result of the changing clinical status of the patient. Table 1 describes the most recent CVVHDF CRRT protocols using citrate for regional anticoagulation. As can be seen, the protocols described by Mehta (10), Kutsogiannis (9), Tobe (8) and Cointault (5) require the use of 4 or more solutions during CRRT. The protocols described by Gabutti (6) and Dorval (7) disclose the use of 3 solutions; however, it should be noted that the citrate solutions require customization of the potassium (Gabutti) or potassium and phosphate levels (Dorval) depending on the clinical status of the individual patients.

The citrate replacement fluid solution, the dialysate solution and the calcium solution described herein are standardized solutions which do not require modification or customization on a per patient basis or during use based on the clinical status of the patient. Furthermore, the standardized replacement fluid, dialysate and calcium solutions are the only three solutions required in order to implement CRRT methods. This is a distinct advantage over many prior art methods which required up to 5 distinct solutions (and which were customized based on individual patient needs). The use of these standardized solutions in CRRT, such as but not limited to CVVHDF, allow for high solute clearance and superior regional anticoagulation properties. Therefore, the novel standardized solutions disclosed herein do not require customization based on the needs of an individual patient. Furthermore, the standardized solutions disclosed herein do not require alterations during use. The standardized solutions achieve metabolic and electrolyte control, as well as a constant effluent rate, by altering solution flow rates rather than by changing the composition of the solutions.

Preparation of Standardized Solutions

The present disclosure provides a novel, standardized citrate replacement fluid solution, a standardized dialysate solution and a standardized calcium solution for use in a variety of CRRT protocols. The solutions are described below.

The present disclosure describes a standardized citrate replacement fluid solution and the use of the citrate replacement fluid solution in CRRT methods. The citrate replacement fluid solution comprises from about 15 to about 25 mmol/L citrate and from about 130-150 mmol/L sodium ($Na^+$). In one embodiment, the sodium is isotonic (about 140 mmol/L). Two embodiments of the citrate replacement fluid solution are described: (i) a 0.67% trisodium citrate (TSC) solution; and (ii) a 0.5% TSC solution. In the first embodiment, the 0.67% TSC replacement fluid solution comprises 23 mmol/L citrate and 140 mmol/L sodium. The 0.67% TSC solution was prepared by pooling the following into an empty 3 L bag: 2500 mL of 0.45% NaCl, 500 mL of 4% citrate (4% TSC Solution; Baxter, McGraw Park, Ill., U.S.A.), and 6 mL of concentrated NaCl (4 mmol/mL). As would be obvious to one of ordinary skill in the art, alternate methods of formulation providing alternate volumes may be used. In the second embodiment, the 0.5% TSC solution comprises 18 mmol/L citrate and 140 mmol/L sodium. The 0.5% citrate solution was prepared by pooling the following into an empty 3 L bag: 2250 mL of 0.45% NaCl, 325 mL of 4% citrate (4% TSC Solution; Baxter, McGraw Park, Ill., U.S.A.), and 15 mL of concentrated NaCl (4 mmol/mL). As would be obvious to one of ordinary skill in the art, alternate methods of formulation providing alternate volumes may be used.

The dialysate solution comprises from about 120 to about 145 mmol/L sodium, from about 110 to about 130 mmol/L chloride ($CL^-$), from about 20 to about 35 mmol bicarbonate ($HCO_3$), from about 2 to about 4 mmol/L potassium ($K+$) and magnesium from about 0.5 to about 0.7 mmol/L. In one embodiment the dialysate solution comprises 140 mmol/L sodium, 118.5 mmol/L chloride, 25 mmol/L bicarbonate, 4.0 mmol/L potassium and 0.58 mmol/L magnesium (referred to as Bicarbonate-25). The dialysate solution was prepared by pooling the following into an empty 4 L bag: 4000 mL of Sterile Water for injection, 240 mL of Normocarb® (Dialysis Solutions Inc, Toronto, Canada), 36 mL of concentrated NaCl (4 mmol/ml), and 9 mL of concentrated KCl (2 mmol/mL). Normocarb® contains 140 mmol/L, chloride 106.5 mmol/L, bicarbonate 35 mmol/L, and Magnesium 0.75 mmol/L. The calcium solution comprises from about 20 to about 50 mmol/L calcium. In one embodiment, the calcium solution is a calcium gluconate solution of 38.75 mmol/L prepared by adding 200 mL of 10% calcium gluconate solution to 1000 mL of 0.9% NaCl. A bicarbonate-based dialysate was used to offset the citrate removed in the effluent [16, 17].

Many methods may be used to formulate solutions described herein. The foregoing is provided as exemplary only and is not meant to exclude other methods of preparation of the solutions.

Description of CRRT Technique

Figure 1B:
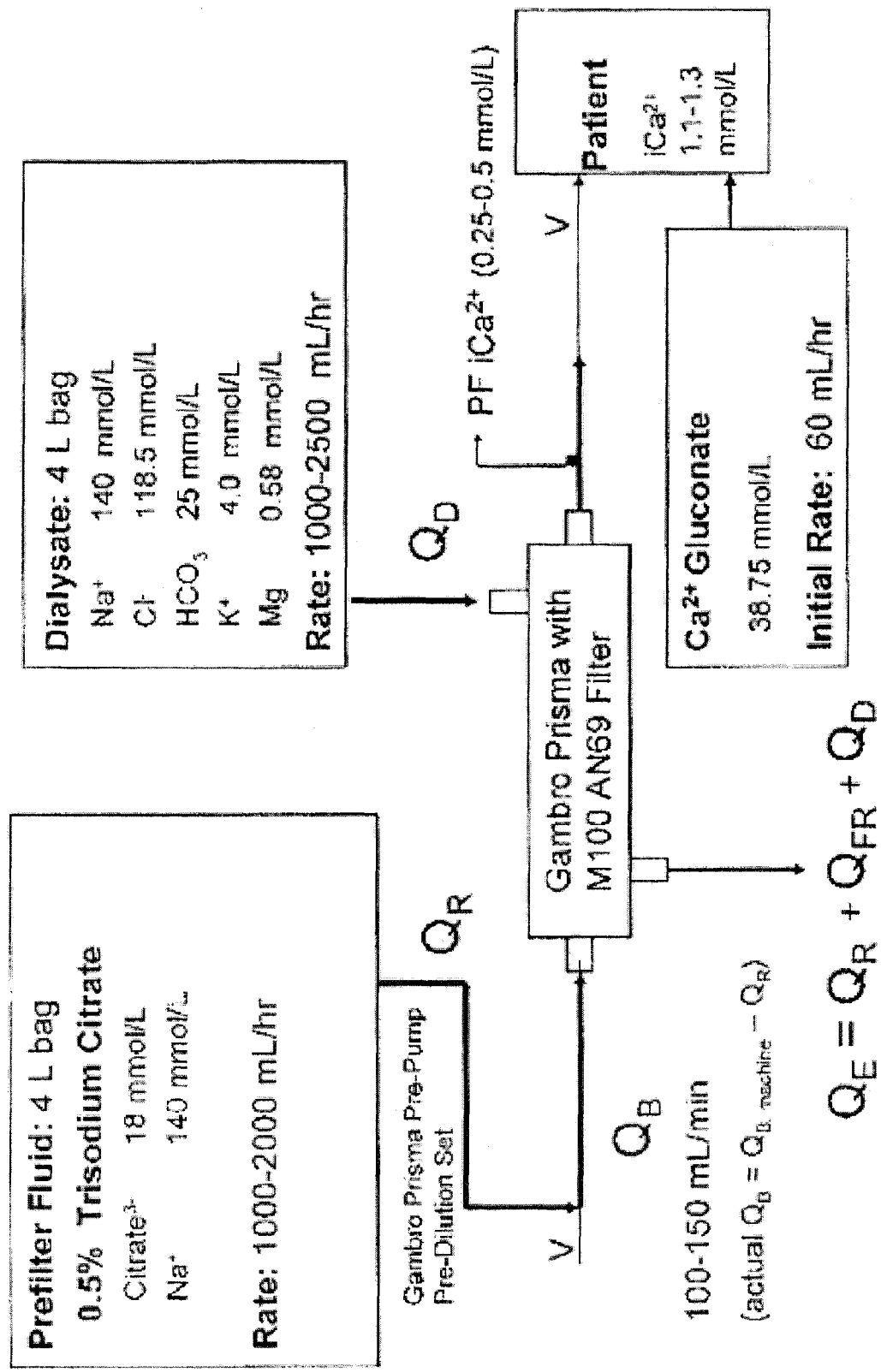
FIG. 1B shows one embodiment of a schematic diagram of the procedure for CVVHDF CRRT therapy using the 0.5% TSC solution as the replacement fluid solution and Bicarbonate-25 as the dialysate solution.

In the embodiment described herein, the CRRT technique was CVVHDF. In one embodiment, CVVHDF was performed using a COBE Prisma pre-pump M100 set with an AN69 dialyzer (effective surface area of 0.9 $m^2$) through a double lumen 12 French catheter inserted into either the internal jugular, subclavian, or femoral vein. FIGS. 1A and 1B illustrate schematically the CRRT protocol using a 0.67% citrate replacement fluid solution (FIG. 1A) and a 0.5% citrate replacement fluid solution (FIG. 1B). The prepump M100 infusion set is commercially available and consists of a simple stopcock and extension line that allows a greater portion of the access line to be diluted by redirecting the citrate replacement fluid solution close to the blood access site and before the blood pump. Such a placement permits anticoagulation of virtually the entire extracorporeal circuit when the citrate replacement solution is delivered pre-filter. Such a placement also maintains filter patency, extending filter life. The calcium solution was administered through a separate central venous line (or through the accessory infusion port of a large bore multi-lumen central venous catheter) Post-filter ionized calcium levels were measured from the post-filter blood sample port (blue in color) located on the return line of the Prisma device to guide the regional citrate dose.

Since the infusion set is routed through the pre-filter replacement fluid port of the Prisma, the citrate replacement fluid solution infusion rate is accounted for by the Prisma device in calculations of net fluid removal. In the embodiment described, hemodiafiltration was accomplished using a blood flow rate of 90-180 mL/min. Other blood flow rates may also be used as is known in the art. In an alternate embodiment, blood flow rates from 50-250 ml/min may be used. The dose of dialysis obtained using the methods described herein may be calculated as is know to one of ordinary skill in the art. In one embodiment, a weight based scheme is used to determine the dose of dialysis. Using the Prisma machine, the total effluent rate in mL/hr is equal to the sum of the replacement fluid rate (mL/hr), dialysate rate (mL/hr), and fluid removal rate (mL/hr). In the embodiment described herein, effluent rates of 35 mL/kg/hr were used and determined by the patient's bodyweight in kilograms at initiation of CVVHDF. Other effluent rates may also be used as would be obvious to one of ordinary skill in the art. In an alternate embodiment, the effluent rates may be from about 20 to about 50 ml/kg/hr. The rate of delivery of the citrate replacement fluid solution and the dialysate solution may be independently varied from about 500 to about 3500 ml/hr. In one embodiment, the rate of delivery of the citrate replacement fluid solution and the dialysate solution are 1000 mL/hr. The rate of delivery may be determined by the healthcare provider based on patient requirements or treatment objectives. The rate of delivery of the calcium solution may be varied from about 10 to about 150 mL/hr. In one embodiment, the rate of delivery of the calcium solution is about 60 mL/hr. The rate of delivery may be determined by the healthcare provider based on patient requirements or treatment objectives.

The rate of delivery of the citrate replacement fluid solution, the dialysate solution and the calcium solution may be titrated from the initial delivery rate as determined by the healthcare provider based on patient requirements or treatment objectives. For example, the citrate replacement fluid solution and the dialysate solution may be titrated from the initial rate in predetermined increments to maintain post-filter ionized calcium levels between 0.25-0.5 mmol/L In one embodiment, the predetermined increments are from about 25 to 200 mL/hr.

The calcium solution may be titrated by in predetermined increments to maintain systemic ionized calcium levels between 0.9-1.3 mmol/L. In one embodiment, the predetermined increments are from about 10 to about 30 mL/hr. For example, if systemic ionized calcium levels in the range of about 0.8 to 0.9 mmol/L, the rate of delivery of the calcium solution may be increased by 10 ml/hr and if the systemic ionized calcium levels are less than about 0.8 mmol/L, the rate of delivery of the calcium solution may be increased by 20 mL/hr. If the systemic ionized calcium were greater than about 1.3 mmol/L, the rate of delivery of the calcium solution may be decreased by 10 ml/hr increments until a therapeutic level was obtained.

In the embodiment described above, the effluent rate (mL/kg/hr) was used as a surrogate for the dose of dialysis and calculated as follows:

Effluent Rate=(Dialysate flow rate (mL/hr)+Replacement fluid flow rate (mL/hr)+Fluid removal rate (mL/hr))/Patient weight (kg)

For example, a 70 kg patient would require a total effluent rate of 2450 mL/hr (70 kg×35 mL/kg/hr). Rates for the replacement fluid solution, dialysate solution, and fluid removal would then be adjusted to achieve an effluent rate of 2,450 mL/hr. In one embodiment, the replacement fluid solution and dialysate solution rates were set equally at initiation of CRRT (for example at >1000 ml/hr) and titrated according to the metabolic, anticoagulation, and fluid balance requirements of the patient. The replacement fluid solution and dialysate solution rates may also be set to differ from one another. However, the total effluent rate remained constant.

In an alternate embodiment, a non-weight based scheme may be used to determine the dose of dialysis. In one example of such a scheme, the delivery rate of replacement fluid solution and dialysate solution may be set at a constant rate, with changes made to the fluid removal rate. For example, the rates of delivery of the replacement fluid solution and the dialysate solution may be set as desired (such as from 500 to 3500 ml/hr) and, depending on desired volume status to be achieved, the fluid removal rate may be adjusted.

Monitoring of CRRT Therapy

Serum and post-filter ionized calcium levels are measured to ensure that post-filter ionized calcium levels are in the range of 0.25 to 0.5 mmol/L and serum ionized calcium levels are in the range of about 0.9 to 1.3 mmol/L. Measurements may be taken as determined by the healthcare providers. In one embodiment, serum and post-filter ionized calcium levels were measured 1 hour after initiation of CRRT and then every six hours thereafter. Arterial blood gases (ABGs), serum electrolytes (including but not limited to, magnesium, calcium, and phosphorous), coagulation parameters, and complete blood count are also measured as determined by the healthcare providers. In one embodiment, these components were measured at least daily. Healthcare providers were instructed to call for serum pH<7.20 or >7.45, bicarbonate<15 or >35 mmol/L, or systemic ionized calcium<0.9 or >1.3 mmol/L. Any changes to the fluid removal flow rate, citrate replacement fluid solution flow rate, or dialysate solution flow rate resulted in reciprocal adjustments to ensure a constant effluent rate of 35 mL/kg/hr. Dialyzer filters were changed routinely every 72 hours per the manufacturer's recommendations. Monitoring for citrate toxicity was performed as previously described (18).

Statistical Analysis

Results are presented as means, medians, and interquartile ranges. Baseline characteristics and outcome measures were compared using the Student's t-test or the Wilcoxon rank-sum test for quantitative variables, and the Pearson Chi-square test or Fisher's Exact test for proportions. Filter survival was compared using Kaplan-Meier survival statistics and the log-rank test. A p value<0.05 was considered statistically significant.

Methods of Treatment

The present disclosure also describes a method of treating an individual having a disease or condition treatable using CRRT and the standardized solutions described herein. In one embodiment, the disease or condition is a renal disease. The renal disease may be, but is not limited to, ARF and CRF. There are a variety of causes that contribute to and/or cause ARF or CRF; such causes include, but are not limited to, nephritis, drug use/overdose, surgical intervention, complications arising in premature infants and neonatal environments, transplant procedures, burns, trauma, sepsis, shock and multi-organ failure (25). In an alternate embodiment, the disease or condition is not a renal disease and may include, but not be limited to, drug use/overdose, correction of severe acid base abnormalities, solute/fluid balance control, congestive heart failure, removal of sepsis mediators or cytokines, cerebral edema states, ARDS, liver support, pancreatitis, and burn management (26). The methods of treatment comprise identifying an individual in need of such treatment and administering to such individual the standardized citrate replacement fluid solution and the standardized dialysate solution using a CRRT protocol. In one embodiment, citrate replacement fluid solution is the 0.67% TSC solution or the 0.5% TSC solution described herein, the dialysate solution is the Bicarbonate-25 solution and the CRRT protocol is a CVVHDF protocol as described herein where the citrate replacement fluid solution is introduced via the extracorporeal circuit. The citrate replacement fluid solution and the dialysate solution are administered at rates of about 500 to 3500 mL/hr and the effluent rate is between 20 and 45 mL/kg/hr. In one embodiment, the citrate is delivered at a rate of about 10-40 mM/hr.

The present disclosure also provides a method of providing regional anti-coagulation during a CRRT procedure using the standardized solutions described herein. The method of providing anti-coagulation comprises identifying an individual in need of such anti-coagulation and administering to such individual the standardized citrate replacement fluid solution and the standardized dialysate solution using a CRRT protocol. In one embodiment, citrate replacement fluid solution is the 0.67% TSC solution or the 0.5% TSC solution described herein, the dialysate solution is the Bicarbonate-25 solution described herein and the CRRT protocol is a CVVHDF protocol as described herein where the citrate replacement fluid solution is introduced via the extracorporeal circuit for the prevention of coagulation. The citrate replacement fluid solution and the dialysate solution are administered at rates of about 500 to 3500 mL/hr and the effluent rate is between 20 and 45 mL/kg/hr. In one embodiment, the citrate is delivered at a rate of about 10-40 mM/hr.

The present disclosure also provides methods for extending the patency of a dialysate filter used during a CRRT procedure using the standardized solutions described herein. The method of extending the patency of a dialysate filter comprises identifying an individual in need of CRRT and administering to such individual the standardized citrate replacement fluid solution and the standardized dialysate solution using a CRRT protocol. In one embodiment, citrate replacement fluid solution is the 0.67% TSC solution or the 0.5% TSC solution described herein, the dialysate solution is the Bicarbonate-25 solution described herein and the CRRT protocol is a CVVHDF protocol as described herein where the citrate replacement fluid solution is introduced via the extracorporeal circuit for the prevention of coagulation. By preventing coagulation of the blood in the extracorporeal circuit, the life of the dialysate filter is extended. In one embodiment, filter patency was greater than 70% after 72 hours of CRRT. The citrate replacement fluid solution and the dialysate solution are administered at rates of about 500 to 3500 mL/hr and the effluent rate is between 20 and 45 mL/kg/hr. In one embodiment, the citrate is delivered at a rate of about 10-40 mM/hr.

EXAMPLES

The present disclosure provides the following Examples to illustrate the teachings of provided herein. The Examples below are to be understood to describe the application of certain embodiments of the technology enabled by the present disclosure and should not be taken as limiting the present disclosure in any manner. The formulations, methods of administration and uses described in the Examples may be modified as would be known to one of ordinary skill in the art and as set forth in the present specification. Additional information regarding the methods used in the present disclosure may be found in (24).

Patient Clinical Characteristics at Initiation of CRRT

Two studies were performed to evaluate the standardized solutions used in conjunction with a CRRT protocol. In one study, the 0.67% TSC solution was used as the citrate replacement fluid solution. In a second study, the 0.5% TSC solution was used as the citrate replacement fluid solution. In both studies the dialysate solution was the Bicarbonate-25 solution.

For the studies using the 0.67% TSC solution, 24 consecutive adult ICU patients with ARF who received CVVHDF from August 2003 to February 2004 at the University of Alabama at Birmingham using 0.67% citrate replacement fluid solution and the dialysate solution (Bicarbonate-25) at an effluent rate of 35 mL/kg/hr were prospectively studied. The CRRT protocols were performed as described herein. For the studies using the 0.5% TSC solution, 32 consecutive ICU patients with ARF who received CVVHDF from May 2004 to June 2005 using the same protocol except that 0.5% citrate replacement fluid solution was used. Patients were eligible for inclusion in either group if they were 19 years of age or older and received at least 48 hours of CRRT. Data collected upon enrollment included demographics, clinical parameters, Acute Physiology and Chronic Health Evaluation (APACHE) II score at initiation of CRRT, serum chemistries, arterial blood gas, and coagulation indices. CRRT data, including blood flow rate, dialysate rate, replacement fluid rate, fluid removal rate, and dialyzer patency, were also recorded daily.

The baseline characteristics of the 24 ICU patients treated with 0.67% citrate replacement fluid solution and the 32 ICU patients treated with 0.5% citrate replacement fluid solution are shown in Table 2. Metabolic and CRRT parameters are also summarized. At the initiation of CRRT, 15 of 24 patients (56%) in the 0.67% citrate group had sepsis, 13 (54%) were oliguric, 21 (88%) were intubated, and 14 (58%) required pressors for hemodynamic support. In the 0.5% citrate group, 13 of 32 patients (41%) had sepsis, 19 (59%) were oliguric, 26 (81%) were intubated, and 16 (50%) required pressors. There were no significant differences among baseline characteristics between the two groups.

Patient Metabolic and Acid-Base Control on CRRT

Figure 2A:
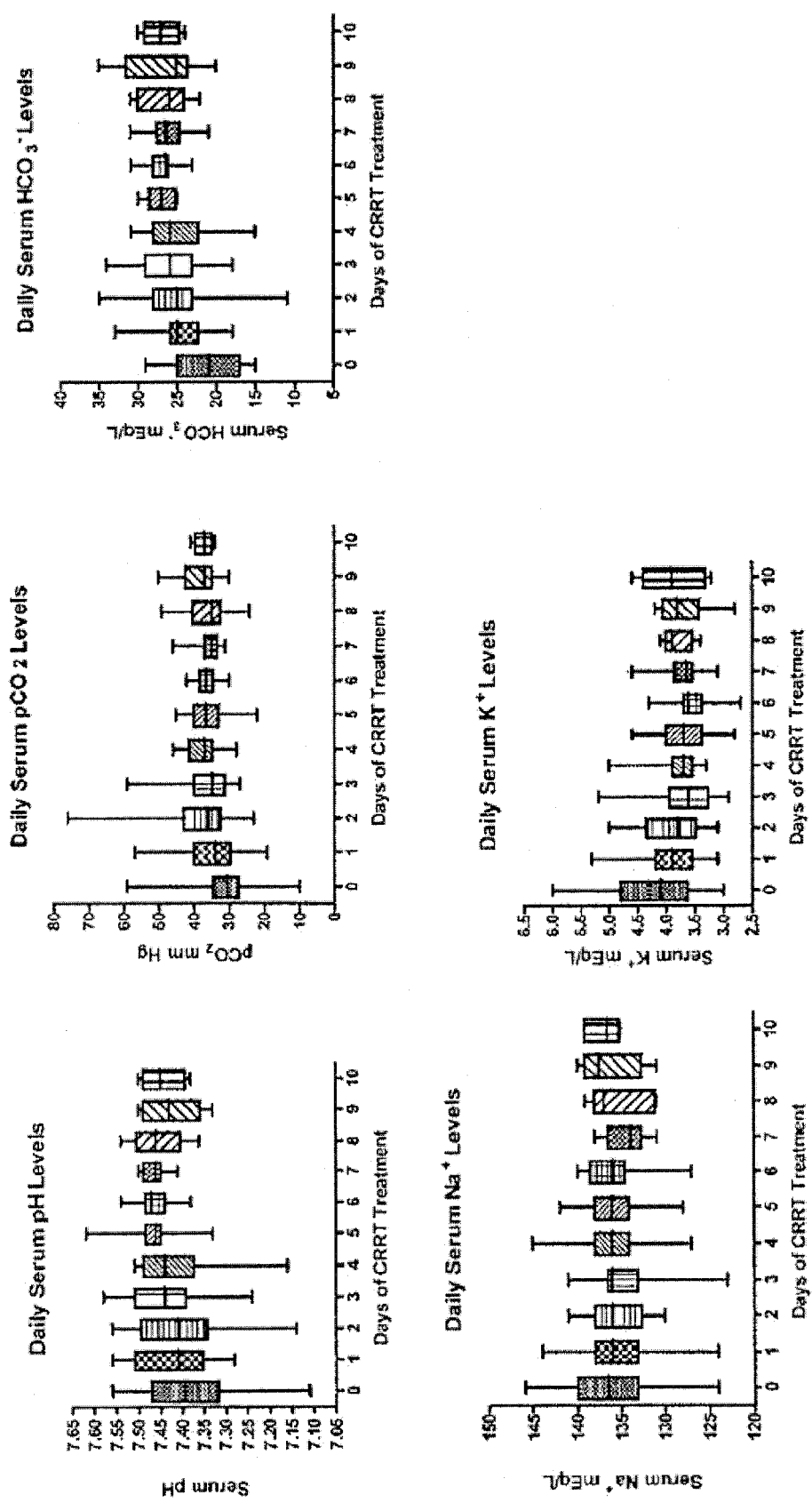
FIG. 2A shows metabolic and electrolyte control for patients treated with CVVHDF CRRT therapy as described herein using the 0.67% TSC solution as the replacement fluid solution and Bicarbonate-25 as the dialysate solution; results are presented as medians and in interquartile ranges.
Figure 2B:
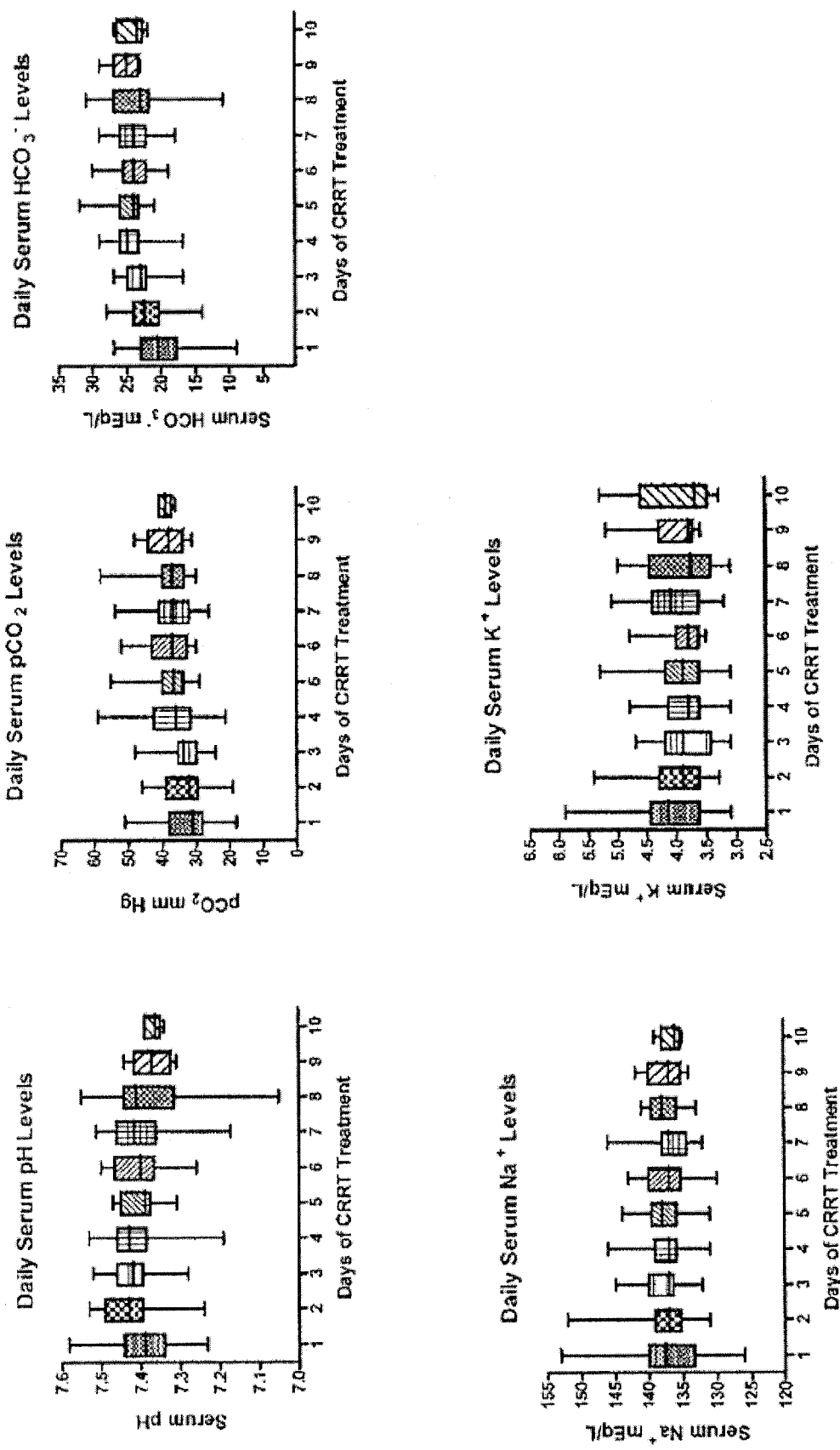
FIG. 2B shows metabolic and electrolyte control for patients treated with CVVHDF CRRT therapy as described herein using the 0.5% TSC solution as the replacement fluid solution and Bicarbonate-25 as the dialysate solution; results are presented as medians and in interquartile ranges.

Acid-base and electrolyte control for the first 10 days of CRRT are shown for both the 0.67% (FIG. 2A) and 0.5% citrate groups (FIG. 2B). The box plot diagrams display median values for pH, pCO2, serum bicarbonate, sodium, and potassium for each day of CRRT, along with interquartile ranges and extreme values. In the 0.67% citrate group, median pH ranged 7.40-7.45. Median serum bicarbonate and pCO2 ranged 21-27 mmol/L and 30-38 mm Hg, respectively. In the 0.5% citrate group, median pH ranged 7.36-7.43. Median serum bicarbonate and pCO2 ranged 21-25 mmol/L and 31-39 mm Hg, respectively.

Metabolic alkalosis during CRRT occurred more frequently in the 0.67% citrate group, compared to the 0.5% citrate group (p=0.001, Chi-square). Eighteen of 24 patients in the 0.67% citrate group had a pH$\geq$7.50 (maximum pH 7.62) at some point during CRRT, while only 9 of 32 patients in the 0.5% citrate group had a pH$\geq$7.50 (maximum pH 7.55). Alkalosis was mitigated by adjusting the rates of the citrate replacement fluid solution and dialysate solution rather than by altering the composition of the standardized solutions as was done in the prior art. For example, to correct metabolic alkalosis (pH$\geq$7.50) in a patient on CRRT with a dialysate solution flow rate of 1500 ml/hr and citrate replacement fluid solution flow rate of 1500 ml/hr, the dialysate solution flow rate may be increased a desired amount and the citrate replacement fluid solution flow rate may be decreased by a corresponding amount to lower the final citrate concentration. For example, in the embodiment where the flow rates for the dialysate solution and the citrate replacement fluid solution are both 1500 mL/hr, the flow rate of the dialysate solution may be increased to 1800 ml/hr and the flow rate for the citrate replacement fluid solution may be decreased to 1200 ml/hr. As discussed above, the effluent rate remains constant as the flow rates underwent corresponding alteration. Decreasing the citrate replacement fluid solution flow rate reduces citrate delivery (and subsequent bicarbonate production) while increasing the flow rate of the dialysate solution (where the bicarbonate concentration is 25 mmol/L for the Bicarbonate-25 dialysate solution) enhances bicarbonate removal, thus lowering the serum bicarbonate levels. Because the dialysate solution is isotonic, problems with significant hypo- or hypernatremia are avoided. None of the patients treated with the 0.67% TSC solution and 3% of the patients treated with the 0.5% TSC solution developed hypernatremia (sodium>150 mmol/L), with the maximum sodium of 153 mmol/L. In comparison, using the prior art 2% citrate replacement fluid solution, 23% of treated patients developed hypernatremia (p<0.01 for both groups, Fisher's Exact test) (19). Potassium levels were normalized using a dialysate potassium bath of 4 mmol/L. Median serum sodium and potassium levels for both the 0.67% and 0.5% TSC solution groups ranged 134-138 mmol/L and 3.6-4.2 mmol/L, respectively. Since bicarbonate-25 dialysate does not contain phosphorous, supplementation with phosphorus was sometimes necessary.

Clotting and Ionized Calcium Data on CRRT

Figure 3:
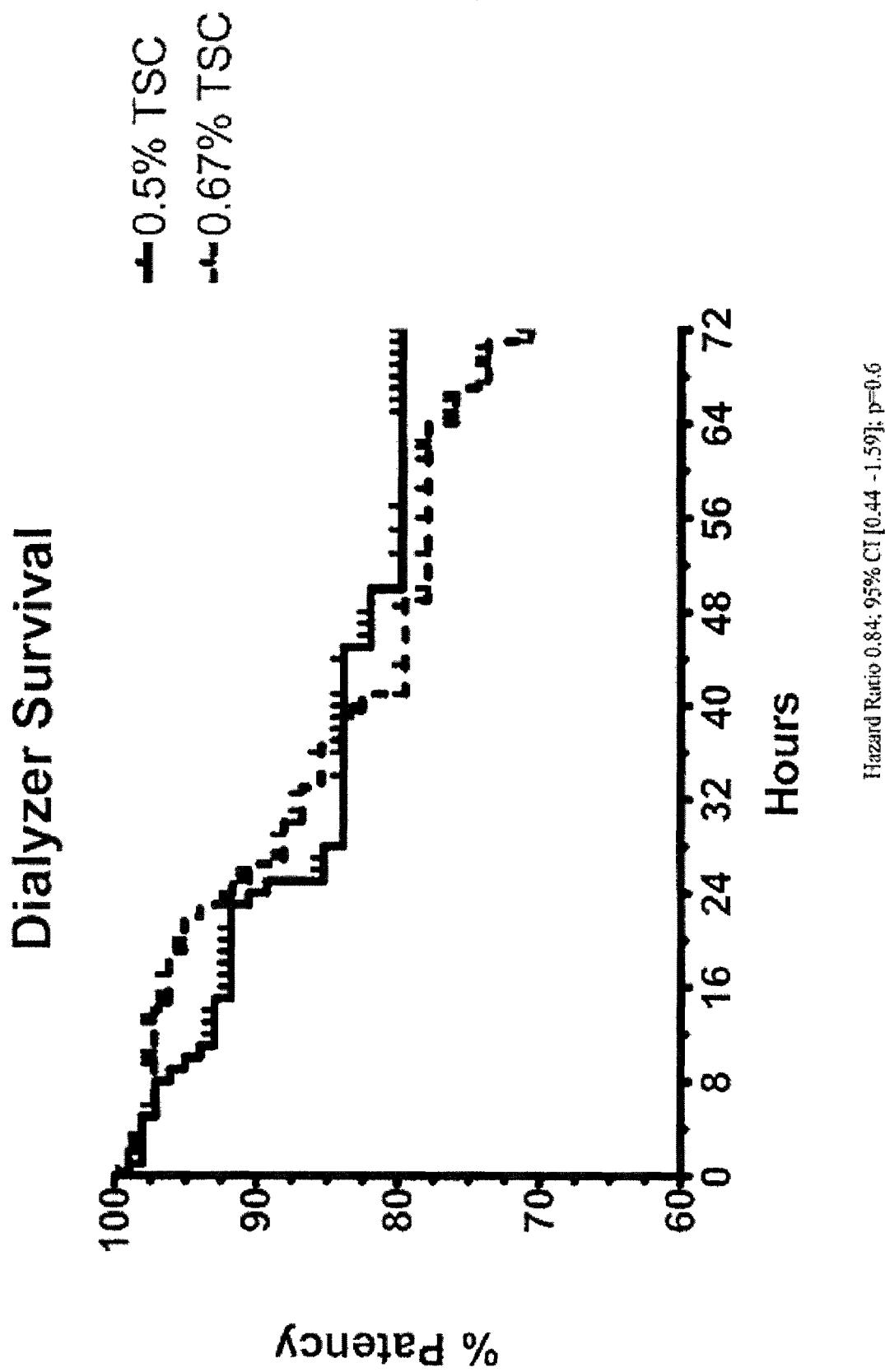
FIG. 3 shows dialyzer filter survival time (patency) for patients treated with CVVHDF CRRT therapy as described herein using the 0.67% TSC solution (dashed line) or 0.5% TSC solution (solid line) as the replacement fluid solution and Bicarbonate-25 as the dialysate solution; results are presented using Kaplan-Meier analysis.

In the patients treated with 0.67% TSC solution (n=24), the mean number of CRRT days per patient was 9.3±8. A total of 111 filters were used. Following initiation of CRRT, 92% of filters were patent at 24 hours, 80% at 48 hours, and 69% at 72 hours (FIG. 3). In the patients treated with 0.5% TSC solution (n=32), the mean number of CRRT days per patient was 7.8±8. A total of 137 filters were used. Eighty-nine percent of filters were patent at 24 hours, 82% at 48 hours, and 80% at 72 hours. There was no significant difference in filter patency between groups. This result is a dramatic increase over that observed using prior art techniques (see Table 1, Circuit Survival Time at 48 hrs).

Systemic ionized calcium levels ranged 0.73-1.45 mmol/L and 0.78-1.54 mmol/L for patients treated with the 0.67% TSC solution and 0.5% TSC solution, respectively. For each abnormal systemic ionized calcium value, adjustment to the calcium solution infusion rate per (as discussed previously herein) resulted in normalization of the ionized calcium level within 1 hour. In the studies presented, there were no instances of clinically significant hypocalcemia, and further adjustments to the infusion rate were minimal once a steady state was achieved. Most adjustments to the systemic calcium solution infusion occurred within 24 hours of CRRT initiation. Despite varying the flow rate of the citrate replacement fluid solution from 900-2000 mL/hr, post-filter ionized calcium levels remained <0.5 mmol/L for both groups, except for one instance which corrected by increasing the replacement fluid rate. Post-filter ionized calcium levels ranged 0.17-0.56 mmol/L and 0.16-0.47 mmol/L for patients treated with the 0.67% TSC solution and 0.5% TSC solution, respectively. There were no bleeding episodes or instances of clinically significant citrate toxicity. The maximum total calcium to ionized calcium ratio was 2.8 for patients treated with the 0.67% TSC solution and 2.7 for patients treated with the 0.5% TSC solution. Overall, both citrate groups received 80% of prescribed CRRT therapy as compared to 68% as described by Venkataram et al (20). Transportation for procedures and patient-care issues, rather than subtherapeutic anticoagulation, mostly contributed to lost treatment time.

Discussion

The use of the standardized solutions in CRRT protocols as described herein provide significant advantages over the prior art. As discussed above, the CRRT methods described utilize only three standardized solutions, thereby greatly reducing the risk of errors in administration and preparation of the solutions. The reduction of such risk is a drawback in using the methods of the prior art (23). In addition, the solutions do not require modification/customization of the solutions based on the clinical status of the patient and the solutions may be used for an entire patient population (thereby achieving significant cost savings in preparation). Therefore, the standardized solutions require no additional modifications. While some prior art CRRT protocols utilize commercial solutions, additives are often adjusted according to an individual's metabolic needs, and sometimes customization is necessary. In contrast, the standardized solutions described herein use standard compositions for the citrate replacement fluid solution, the dialysate solution (which is now commercially available), and the calcium solution. Following initiation of CRRT, the composition of each solution remains unchanged. This allows for batch preparation of solutions, and batch testing, by an admixture pharmacy unit. If CRRT is discontinued, unused solutions are available for other patients and not discarded.

The use of the standardized solutions in CRRT protocols as described herein also provides additional benefits.

The use of the citrate replacement solutions in CRRT methods consistently provided high solute clearance. As shown in Table 1, dialysis dose rates of 1-2 liters per hour were obtained. Recent data suggest that a higher dialysis doses lead to improved clinical outcomes. Schiffl et al demonstrated this finding for intermittent hemodialysis, and Ronco et al confirmed this using CVVH (21, 2). In one embodiment used herein, the flow rate of citrate replacement fluid solution and dialysate solution were adjusted to compensate for changes in the fluid removal rate and thereby maintain an effluent rate of 35 ml/kg/hr (determined in part based on the weight of the patient).

However, other protocols may be used. As not all nephrologists use a weight-based protocol or maintain a constant effluent rate, the citrate replacement fluid solution and the dialysate solution may be initiated at a set initial flow rate (such as >1000 ml/hr) and adjusted according to the discretion of the healthcare provider. As a result, the only changes usually required on a daily basis, depending on desired volume status, are to the fluid removal rate. Even without a weight-based dose, excellent metabolic control and high solute clearance are achieved.

The electrolytes in the standardized solution are present at physiologic concentrations, minimizing the risk of metabolic catastrophe in a patient. For instance, even switching the citrate replacement fluid solution and the dialysate solution will not result in a metabolic catastrophe as is the case in prior art solutions for use with CRRT. Imagine the metabolic consequences of inadvertently substituting a concentrated citrate solution (4% TSC) when used as the replacement fluid solution, where the sodium concentration in commercially available solutions may be as high as 408 mmol/L (9, 10), for the dialysate solution, and then increasing the flow rate from 200 mL/hr (a common rate for 4% TSC replacement fluid solution) to 1000 mL/hr (a common rate for dialysate solution). Problems may also be encountered when using concentrated citrate for anticoagulation and a low-sodium dialysate, as per Mehta's protocol (10). If the citrate replacement fluid solution is omitted, or the low sodium dialysate mistakenly substituted for the citrate replacement fluid solution, the resulting hyponatremia may be fatal. Using the standardized solutions of citrate replacement fluid and dialysate as described herein, any accidental interchanges of the dialysate and citrate replacement fluid solutions, or their respective rates, results in negligible metabolic consequences due to the dilute citrate concentration and physiologic content of electrolytes.

When using the 0.5% TSC solution as the citrate replacement fluid solution, citrate concentration in the range of 2-6 mmol/L was observed with citrate replacement fluid solution flow rates ranging 1-2 L/hr. It has previously been demonstrated that a blood citrate concentration of 3-6 mmol/L corresponds to a systemic ionized calcium level<0.35 mmol/L (22). Table 3 illustrates the blood citrate concentration for varying blood flow and replacement fluid rates using the 0.5% citrate protocol. For ranges in blood flow rates between 100-180 mL/min and replacement fluid rates between 1-2 L/hr, ionized calcium levels are easily maintained <0.5 mmol/L. Therefore, metabolic complications using the standardized citrate replacement fluid solution are minimized.

Four of the CRRT protocols incorporating citrate (see Table 1) use a three-way stopcock or Y-connector (5, 8, 9, 10) placed at the end of the arterial limb of the venous access for the citrate infusion. In these protocols, the replacement fluid solution is administered as usual through the pre-filter replacement fluid port on the dialysis device. Since the stopcock is outside of the CRRT circuit, net fluid removal measured by the CRRT device does not include the citrate infusion rate. Thus, the healthcare provider, such as the nursing staff, becomes responsible for including the amount of citrate infused when net fluid balance is calculated. As the present disclosure includes citrate in the replacement fluid solution and the citrate replacement fluid solution is added at the pre-filter replacement port, the citrate infusion calculations are accounted for by the dialysis device in calculations of net fluid removal. This procedure simplifies the tasks for healthcare providers and minimizes the risk of error in administration of CRRT therapy.

Only two protocols use dilute citrate and a total of 3 solutions (6, 7) (see Gabutti and Dorval in Table 1). In 2003, Dorval et al (7) prospectively evaluated 14 patients over 72 hours using a citrate anticoagulation regimen for CVVHDF. While Dorval et al. showed that a citrate containing replacement fluid solution simplified CRRT, only 4 of 14 patients actually received a dialysate (and thus CVVHDF), and the rest received CVVH (without a dialysate). Potassium and phosphorus were added to the replacement fluid as needed, according to patient requirements, thereby requiring customization of the solutions. Additionally, the ultrafiltration rate was limited to 2 L/hr, due to the risk of citrate toxicity. Gabutti et al (6) evaluated 12 patients using dilute citrate in both the replacement fluid solution (13.3 mmol/L) and dialysate solution (13.3 mmol/L). In their approach, the compositions of the dialysate solution and/or citrate replacement fluid solution were titrated based on systemic pH again requiring modification of the components of the solutions. While the protocol simplified citrate use with CVVHDF, it was limited by having to reduce the dialysate and ultrafiltration rates at high pH, since both solutions contained citrate. As a result, some patients with a high pH received only replacement fluid and no dialysate. Furthermore, five patients were switched from citrate to heparin for uncertain reasons, and the ultrafiltration rate for all patients was limited to 2 L/hr. Finally, filter survival was only 15% at 48 hours.

The remaining citrate protocols shown in Table 1 are more complicated, require additional solutions and mixtures, and have lower filter survival rates as compared to CRRT using the standardized solutions of the present disclosure. Some patients receiving 0.67% citrate developed mild alkalosis and required adjustment to the replacement fluid solution flow rate and dialysate solution flow rate for correction. Alkalosis was later mitigated in the second patient cohort by dilution of the citrate replacement fluid solution to 0.5%. With 0.5% citrate, changes to the replacement fluid solution flow rate and dialysate solution flow rate only occurred if the fluid removal rate was altered, in order to keep the effluent rate at the desired level (in the Examples at 35 mL/kg/hr). Since acid-base status was adequately controlled with the 0.5% solution, further rate adjustments were unnecessary.

Use of the standardized citrate replacement fluid solution and the dialysate solution in CRRT permitted significant cost curtailment in the delivery of CRRT. This has largely resulted from standardization of solutions, less waste, and fewer dialyzer changes for clotting. The solution cost for CRRT at the Applicants' center, per patient per day, has declined from $370 to $290 between 1999 and 2005, mainly from reduced pharmacy costs and the commercial availability of the dialysate solution (Gambro, Lakewood, Colo. USA). Furthermore, use of the standardized citrate replacement fluid solution and the dialysate solution in CRRT was shown to provide effective metabolic control, high ultrafiltration rates, and anticoagulation of the CRRT circuit, without increasing the risk of citrate toxicity. Changes in the composition of the citrate replacement fluid solution and the dialysate solution are avoided, thereby containing cost, reducing workload, and minimizing errors. Furthermore, the risk of adverse patient events, such as bleeding and metabolic catastrophe, is negligible. The standardized citrate replacement fluid solution and the dialysate solution are simple to produce and versatile in that they can be used for the entire patient population. Therefore, the use of the standardized citrate replacement fluid solution and the dialysate solution provides a safe, effective, and practical alternative to the replacement fluid solutions and dialysate solution presently available in the art and represent a significant step toward the more widespread acceptance of CRRT as the modality of choice for renal replacement in critically ill patients.

References

1. Clark W R, Murphy M H, Alaka K J, Mueller B A, Pastan S O, Macias W L: Urea kinetics during continuous hemofiltration. *ASAIO J* 38: M664-667. 1992
2. Ronco C, Zanella M, Brendolan A, Milan M, Canato G, Zamperetti N, Bellomo R: Management of severe acute renal failure in critically ill patients: an international survey in 345 centres. *Neph Dial Trans* 16: 230-237. 2001
3. Ronco C, Bellomo R, Homel P, Brendolan A, Dan M, Piccinni P, La Greca G: Effects of different doses in continuous veno-venous haemofiltration on outcomes of acute renal failure: a prospective randomized trial. *Lancet* 355: 26-30. 2000
4. Monchi M, Berghmans D, Ledoux D, Canivet J L, Dubois B, Damas P: Citrate versus heparin for anticoagulation in continuous venovenous hemofiltration: a prospective randomized study. *Intensive Care Med* 30: 260-265. 2004
5. Cointault O, Kamar N, Bories P, Lavayssiere L, Angles O, Rostaing L, Genestal M, Durand D: Regional citrate anticoagulation in continuous venovenous haemodiafiltration using commercial solutions. *Neph Dial Trans* 19:171-178. 2004
6. Gabutti L, Marone C, Colucci G, Duchini F, Schonholzer C: Citrate anticoagulation in continuous venovenous hemodiafiltration: a metabolic challenge. *Intensive Care Med* 28:1419-1425. 2002
7. Dorval M, Madore F, Courteau S, Leblanc M: A novel citrate anticoagulation regimen for continuous venovenous hemodiafiltration. *Intensive Care Med* 29:1186-1189. 2003
8. Tobe S W, Aujla P, Walele A A, Oliver M J, Naimark D M, Perkins N S, Beardsall M: A novel regional citrate anticoagulation protocol for CRRT using only commercially available solutions. *J Crit Care* 18: 121-129. 2003
9. Kutsogiannis D, Mayers I, Chin W D, Gibney R T: Regional citrate anticoagulation in continuous venovenous hemodiafiltration. *AJKD* 35: 802-811. 2000
10. Mehta R L, McDonald B R, Aguilar M M, Ward D M: Regional citrate anticoagulation for continuous arteriovenous hemodialysis in critically ill patients. *Kidney Int* 38: 976 981. 1990
11. Mueller B A: Pharmacy aspects of Continuous Renal Replacement Therapies. 2004 Midyear Clinical Meeting, College of Pharmacy, University of Michigan. http://ashp.omnibooksonline.com/2004/papers/PI-009.pdf
12. External Patient Safety Review, Calgary Health Region, June 2004
13. Canada News Wire Group: Health Quality Council of Alberta releases recommendations for safe handling of potassium chloride containing products and preparation of continuous renal replacement therapy dialysis solutions in hospitals. July, 2004
14. Mehta R: Continuous renal replacement therapy in the critically ill patient. *Kidney Int* 67: 781-795. 2005
15. Tolwani A, Campbell R, Schenk M, Allon M, Warnock D G: Simplified citrate anticoagulation for continuous renal replacement therapy. *Kidney Int* 60:370-374. 2001
16. Swartz R, Pasko D, O'Toole J, Starmann B: Improving the delivery of continuous renal replacement therapy using regional citrate anticoagulation. *Clin Nephrol* 61:134 143. 2004
17. Chadha V, Garg U, Warady B A, Alon U S: Citrate clearance in children receiving continuous venovenous renal replacement therapy. *Pediatr Nephrol* 17: 819-824. 2004
18. Meier-Kriesche H U, Finkel K W, Gitomer J J, DuBose T D Jr.: Unexpected severe hypocalcemia during continuous venovenous hemodialysis with regional citrate anticoagulation. *Am J Kidney Dis* 33: 1-4. 1999
19. Walker L J, Campbell R C, O'Reilly P J, Tolwani A J. Continuous renal replacement therapy using 2% trisodium citrate regional anticoagulation: a prospective study [Abstract]. *Blood Purif* 19: 333. 2001
20. Venkataraman R, Kellum J A, Palevsky P: Dosing patterns for continuous renal replacement therapy at a large academic medical center in the United States. *J Crit Care* 17: 246-250. 2002
21. Schiffl H, Lang S M, Fischer R: Daily hemodialysis and the outcome of acute renal failure. *NEJM* 346: 305-310. 2002
22. Flanigan M J, Pillsbury L, Sadewasser G, Lim V S: Regional hemodialysis anticoagulation: hypertonic trisodium citrate or anticoagualation citrate dextrose. *Am J Kidney Dis* 27: 519-524. 1996
23. Mehta R: Acid-base and electrolyte management in continuous renal replacement therapy. *Blood Purif* 20: 262-268. 2002
24. Tolwani A J, Predergast, M B, Speer, R R, Stofan B S, Wille, K M: A Practical Citrate Anticoagulation CVVHDF Protocol for Metabolic Control and High Solute Clearance. *Clin J Am Soc Nephrol* In Press. 2005
25. Ronco C, Zanella M, Brendolan A, Milan M, Canato G, Zamperetti N, Bellomo R: Management of severe acute renal failure in critically ill patients: an international survey in 345 centers. *Nephrol Dial Transplant* 16:230-237. 2001
26. Vanholder R, Biesen W V, Lameire N: What is the renal replacement method of first choice for intensive care patients? *J Am Soc Nephrol* 12:S40-S43. 2001

TABLE 1

Comparison of CRRT Protocols Using Regional Citrate Anticoagulation

| Year/Author | Pt. # | BFR* (mL/min) | Citrate Solution (mM/L) | Citrate Rate | Replacement Solution (mM/L) | Repl. Solution Flow Rate | Dialysate Composition (mM/L) | D** Rate | Ca Solution (mM of elemental Ca/L) | Calcium Rate | Circuit Survival Time 48 hrs | # CRRT Solutions |
|---|---|---|---|---|---|---|---|---|---|---|---|---|
| Mehta 1990 | 18 | 100 | TSC+ 4% Citrate 140 Na 408 | 140-220 mL/hr (19.6-30.8 mM/hr) | Pre-filter: NS 0.9% Post-filter: NS 0.9% and Variable | Pre-filter: 500 mL/hr Post-filter: 0.2-1.5 L/hr | NA 117 Cl 81-121 K 0-4 Mg 1 Dextrose 0.1% HCO3 0-40 | 1 L/hr | CaCl 0.8% | 40-60 mL/hr | 68% | 5 |
| Kutsogiannis 2000 | 9 | 100-125 | TSC 4% Citrate 140 Na 408 | 140-190 mL/hr (19.6-26.6 mM/hr) | Pre-filter: Na 150.3 Cl 121 HCO3 33.3 K 3-4 Mg 0.7 | Pre-filter: 1-1.5 L/hr | Na 117 Cl 121.5 K 3-4 Mg 0.7 | 1-1.5 L/hr | CaCl 0.75% | 40-60 mL/hr | 68% | 4 |
| Gabutti* 2002 | 12 | 150 | Citrate 13.3 Na 139.9 Mg 0.75 (K as needed) | 1.5 L/hr (23 mM/hr) | See citrate solution | See citrate solution | Citrate 13.3 Na 139.9 Mg 0.75 (K as needed) | 500 mL/hr | 5% CaCl or 350 mM/L | Mean rate: 10 mL/hr or 3.31 mM/hr | 15% | 3 |
| Dorval* 2003 | 14 | 125 | Hemocitrasol-20 Na 145 Citrate 20 Glucose 10 (K and PO4 as needed) | 1.25 L/hr (25 mM/hr) | See citrate solution | See citrate solution | (Dialysate added in only 27% patients) NS 0.9% Na 154 | 1 L/hr prn | Mg 16 mM/L & 1% CaCl 70 mM/L | 50 mL/hr or 3.5 mM/hr | 50% | 3 |
| Tobe 2003 | 15 | 100 | ACD-A ® Citrate 113 Na 224 | 150 mL/hr (17 mM/hr) | Pre-filter: NS 0.9% or ½ NS | 0-1 L (started for HCO3 >25) | Normocarb ® Na 140 HCO3 35 Cl 106.5 Mg 0.75 (K as needed) | 1-1.5 L/hr | CaCl 4 gms in 1 L D5W | 50 mL/hr | ~50% | 4 |
| Cointault* 2004 | 17 | 125 | ACD-A ® Citrate 113 Na 224 | 250 mL/hr ~(30 mM/hr) | Pre-filter: Hemosol & Hemosol with Bicarbonate Na 144 HCO3 35 Lactate 3 Mg 0.5 Calcium 1.75 (mixture of 2 solutions) For Peer Review | 1.2 L/hr | Hemosol & Hemosol with Bicarbonate Na 144 HCO3 35 Lactate 3 Mg 0.5 Ca 1.75 (mixture of solutions are varied to | 1.2 L/hr | CaCl 45.6 mM/L | 30 mL/hr or 1.37 mM/hr | 41% | 4 |
| Tolwani 2005 | 32 | 100-150 | TSC 0.5% Citrate 18 Na 140 | 1-1.5 L/hr (18-27 mM/hr) | See citrate solution | See citrate solution | | | | | | |

TABLE 1-continued

Comparison of CRRT Protocols Using Regional Citrate Anticoagulation

| | | | | | | |
|---|---|---|---|---|---|---|
| Tolwani 2005 | adjust bicarbonate) Na 140 K 4 HCO3 25 Mg 0.58 (similar solution commercially available) | 1-2 L/hr | Ca Gluconate 38.75 mM/L | 60 mL/hr or 2.3 mM/hr | 82% | 3 |

TABLE 2

Clinical characteristics of Patients on CVVHDF * (values are presented as means ± standard deviation)

| | 0.67% Citrate | 0.5% Citrate |
|---|---|---|
| Patients | N = 24 | N = 32 |
| Mean age (years) | 63 ± 15 | 59 ± 16 |
| Male:Female | 11:13 | 22:10 |
| Etiology of ARF | | |
| Sepsis | 15 | 14 |
| Surgery | 5 | 1 |
| Cardiogenic/others | 4 | 17 |
| Mean APACHE II ** | 26 ± 6 | 26 ± 6 |
| Mean weight (kg) | 95 ± 15 | 90 ± 19 |
| Mean BUN (mg/dL) ** | 91 ± 37 | 73 ± 35 |
| Mean Creatinine (mg/dL) ** | 4.2 ± 1.4 | 4.3 ± 1.6 |
| Mean pH ** | 7.33 ± 0.1 | 7.34 ± 0.09 |
| Mean pCO2 (mmHg) ** | 33 ± 11 | 34 ± 9 |
| Mean HCO3 (mmol/L) ** | 19 ± 5 | 19 ± 5 |
| Mean Na (mmol/L) ** | 139 ± 7 | 137 ± 7 |
| Mean K (mmol/L) ** | 4.5 ± 1.0 | 4.4 ± 0.8 |
| CRRT characteristics | | |
| Mean days of CRRT/patient | 9.3 ± 8 | 7.8 ± 8 |
| Mean CRRT effluent rate (mL/kg/hr) | 35 | 35 |
| Mean blood flow (mL/min) | 117 ± 12 | 116 ± 13 |
| Mean replacement fluid rate (mL/hr) | 1200 ± 229 | 1211 ± 240 |
| Mean fluid removal rate (mL/hr) | 186 ± 57 | 129 ± 64 |
| Mean dialysate rate (mL/hr) | 1919 ± 437 | 1775 ± 542 |

* For all comparisons between groups, p = NS
** At initiation of CRRT

TABLE 3

Blood Citrate Concentration for Varying Blood Flow Rates and Citrate Replacement Fluid Solution Flow Rates Using 0.5% TSC Solution

| Blood Flow Rate (ml/min) | Citrate** (mmol/L) at RF* 1 L/hr | Citrate (mmol/L) at RF 1.5 L/hr | Citrate (mmol/L) at RF 2 L/hr |
|---|---|---|---|
| 100 | 3 | 4.5 | 6 |
| 120 | 2.5 | 3.75 | 5 |
| 150 | 2 | 3 | 4 |
| 180 | 1.7 | 2.5 | 3.3 |
| 200 | 1.5 | 2.25 | 3 |

*RF = citrate replacement fluid solution flow rate
**A blood concentration of citrate of 3-6 mmol/L corresponds to a systemic ionized calcium concentration less than 0.35 mmol/L

We claim:

1. A method of providing CRRT comprising:
   (a) introducing a replacement fluid into an extracorporeal circuit upstream of a dialysis filter, the replacement fluid comprising about 15-25 mM citrate and about 130-150 mM sodium; and
   (b) contacting the dialysis filter with a dialysate fluid comprising about 20-35 mM bicarbonate.

2. The method of claim 1, further comprising introducing a calcium solution into the extracorporeal circuit downstream of the dialysis filter.

3. The method of claim 1, further comprising introducing a calcium solution into the extracorporeal circuit downstream of the dialysis filter, wherein the calcium solution comprises about 20-50 mM calcium.

4. The method of claim 1, wherein the dialysate fluid contains no significant amount of anticoagulant.

5. The method of claim 1, wherein the dialysate fluid further comprises potassium and magnesium.

6. The method of claim 1, wherein the dialysate fluid comprises about 2-4 mM potassium and about 0.5-0.7 mM magnesium.

7. The method of claim 1, comprising introducing the replacement fluid solution at a first flow rate.

8. The method of claim 1 where said replacement fluid solution consists essentially of either:
   (a) 18 mM citrate and 140 mM sodium, or
   (b) 23 mM citrate and 140 mM sodium.

9. The method of claim 7 where said first flow rate is set so as to deliver citrate at a rate of about 18-27 mmol/hr.

10. The method of claim 7 where said first flow rate is about 500 to 3500 mL/hr.

11. The method of claim 7 where a patient receiving CRRT maintains a bicarbonate level of between 15 mM and 35 mM, a serum ionized calcium level of between 0.9 mM and 1.3 mM and a post-filter ionized calcium level of less than 0.5 mM.

12. The method of claim 1 where the filter maintains a filter patency after 72 hours of CRRT of at least about 70%.

13. The method of claim 1 where said replacement fluid solution does not require modification based on the clinical status of the patient.

14. A method of providing CRRT comprising introducing a replacement fluid into an extracorporeal circuit upstream of a dialysis filter, the replacement fluid consisting essentially of about 15-25 mM citrate and about 130-150 mM sodium; and contacting the dialysis filter with a dialysate fluid comprising bicarbonate.

15. The method of claim 14 wherein the dialysate fluid comprises about 110-130 mM chloride, about 20-35 mM bicarbonate, and contains no significant amount of anticoagulant.

16. The method of claim 14, further comprising introducing a calcium solution into the extracorporeal circuit downstream of the dialysis filter.

17. The method of claim 16 wherein the calcium solution comprises about 20-50 mM calcium.

18. The method of claim 16, wherein the calcium solution consists essentially of 20-50 mM calcium.

19. The method of claim 14, wherein the dialysate fluid contains no significant amount of heparin or citrate.

20. The method of claim 14, wherein the dialysate fluid further comprises potassium and magnesium.

21. The method of claim 20, wherein the dialysate fluid comprises about 2-4 mM potassium and about 0.5-0.7 mM magnesium.

22. The method of claim 14, comprising introducing the replacement fluid solution at a first flow rate.

23. The method of claim 14 where said replacement fluid solution consists essentially of either:
(a) 18 mmol/L citrate and 140 mmol/L sodium, or
(b) 23 mmol/L citrate and 140 mmol/L sodium.

24. The method of claim 22 where said first flow rate is set so as to deliver citrate at a rate of about 18-27 mmol/hr.

25. The method of claim 22 where said first flow rate is about 500 to 3500 mL/hr.

26. The method of claim 22 where a patient receiving CRRT maintains a bicarbonate level of between 15 mM and 35 mM, a serum ionized calcium level of between 0.9 mM and 1.3 mM, and a post-filter ionized calcium level of less than 0.5 mM.

27. The method of claim 15 where the filter maintains a filter patency after 72 hours of CRRT of at least about 70%.

28. The method of claim 15 where said replacement fluid solution does not require modification based on the clinical status of the patient.

29. A method of providing CRRT, said method comprising the steps of:
(a) introducing a standardized citrate replacement fluid solution at a first flow rate into the extracorporeal circuit of a dialysis unit and upstream of a filter, and said replacement fluid solution comprising about 15-25 mM citrate and about 130-150 mM sodium;
(b) introducing a standardized dialysate solution at a second flow rate, said dialysate solution comprising about 20-35 mM bicarbonate;
(c) introducing a standardized calcium solution into the extracorporeal circuit downstream of the filter at a fourth flow rate; and
(d) removing fluid from said dialysis unit at a third flow rate.

30. The method of claim 29 where the first, second and third flow rates are independently adjusted to maintain a constant effluent rate.

31. The method of claim 29 where said first, second and third flow rates are independently set so as to maintain an effluent rate of about 20-45 mL/kg/hr, where said effluent rate is determined by adding the first flow rate, the second flow rate and the third flow rate to obtain a sum and dividing said sum by a body weight of said patient.

32. The method of claim 29 where said first and second flow rates are independently set at about 500-3500 mL/hr.

33. The method of claim 29 where said replacement fluid solution comprises either:
(a) 18 mM citrate and 140 mM sodium, or
(b) 23 mM citrate and 140 mM sodium.

34. The method of claim 29, wherein the dialysate solution further comprises potassium and magnesium.

35. The method of claim 34 where said dialysate solution comprises about 140 mM sodium, about 118.5 mM chloride, about 25 mM bicarbonate, about 4.0 mM potassium and about 0.58 mM magnesium.

36. The method of claim 29 where said first flow rate is set so as to deliver citrate at a rate of about 18-27 mmol/hr.

37. The method of claim 29 where a patient receiving CRRT maintains a bicarbonate level of 15-35 mM, a serum ionized calcium level of 0.9-1.3 mM, and a post-filter ionized calcium level of less than 0.5 mM.

38. The method of claim 29 where said filter maintains a filter patency after 72 hours of at least about 70%.

39. The method of claim 29 where said replacement fluid solution and said dialysate solution do not require modification based on the clinical status of the patient.

40. The method of claim 1, wherein the dialysate fluid comprises about 110-130 mM chloride.

41. The method of claim 29, wherein the dialysate solution comprises about 110-130 mM chloride.

* * * * *